United States Patent [19]

Chiba et al.

[11] 4,300,991
[45] Nov. 17, 1981

[54] AIR-FUEL RATIO DETECTING APPARATUS

[75] Inventors: Masao Chiba, Chigasaki; Takeshi Fujishiro, Yokosuka, both of Japan

[73] Assignee: Nissan Motor Company, Limited, Yokohama, Japan

[21] Appl. No.: 158,379

[22] Filed: Jun. 11, 1980

[30] Foreign Application Priority Data

Jun. 13, 1979 [JP] Japan .................................. 54-73509

[51] Int. Cl.$^3$ .............................................. G01N 27/58
[52] U.S. Cl. .................................................. 204/195 S
[58] Field of Search ............................. 204/195 S, 1 S

[56] References Cited

U.S. PATENT DOCUMENTS 4,207,159 6/1980 Kimura et al. .................... 204/195 S
4,224,113 9/1980 Kimura et al. ........................ 204/1 T

FOREIGN PATENT DOCUMENTS 2631819 1/1978 Fed. Rep. of Germany .

Primary Examiner—G. L. Kaplan
Attorney, Agent, or Firm—Schwartz, Jeffery, Schwaab, Mack, Blumenthal & Koch

[57] ABSTRACT

An air-fuel ratio detecting apparatus, comprises a first pair of electrodes, interposing a porous solid electrolyte therebetween, a second pair of electrodes, interposing a porous solid electrolyte therebetween, a dense solid electrolyte to which one of the first pair of electrodes and one of the second pair of electrodes contact, and a device for causing constant-currents to flow through the first and second pairs of electrodes, respectively, so as to detect voltage developed between the electrodes contacting with the dense solid electrolyte, thereby for obtaining air-fuel ratio detecting apparatus having uniform voltage output characteristics even by mass production.

15 Claims, 9 Drawing Figures

AIR-FUEL RATIO DETECTING APPARATUS

FIELD OF THE INVENTION

This invention relates to an air-fuel ratio detecting apparatus for detecting the air-fuel ratio at a rich or lean air-fuel mixture (combustion gas) range, by sensing the amount of oxygen present in engine exhaust gas.

BRIEF SUMMARY OF THE INVENTION

In accordance with the present invention, an air-fuel ratio detecting apparatus comprises a piled layer sensing body which is constructed of a first pair of electrodes, a porous solid electrolyte interposed therebetween, and a second pair of electrodes, having a porous solid electrolyte interposed therebetween. A dense solid electrolyte is further provided so that one of the first pair of electrodes and one of the second pair of electrodes are in contact therewith. Furthermore, the detecting apparatus further comprises a device for causing constant-currents to flow through the first and second pairs of electrodes, respectively, so as to detect voltage developed between the electrodes contacting the dense electrolyte layer.

An object of the present invention is to provide an improved air-fuel ratio detecting apparatus which is higher in accuracy in detecting air-fuel ratio both on the rich and lean air-fuel mixture sides, overcoming drawbacks encountered in conventional corresponding apparatus.

Another object of the present invention is to provide an improved air-fuel ratio detecting apparatus, by which air-fuel ratio detecting apparatuses having uniform characteristics can be obtained even by mass production.

A further object of the present invention is to provide an improved air-fuel ratio detecting apparatus using solid electrolytes, by which air-fuel ratio detecting apparatuses exhibit uniform voltage output characteristics even though scattering in resistance value of the electrolytes arises during mass production, without use of means for making the output voltage of the solid electrolyte constant.

BRIEF DESCRIPTION OF THE DRAWINGS

The features and advantages of the air-fuel ratio detecting apparatus according to the present invention will be more clearly appreciated from the following description taken in conjunction with the accompanying drawings in which like reference numerals designate the corresponding parts and elements, and in which.

BACKGROUND OF THE INVENTION

Figure 1:
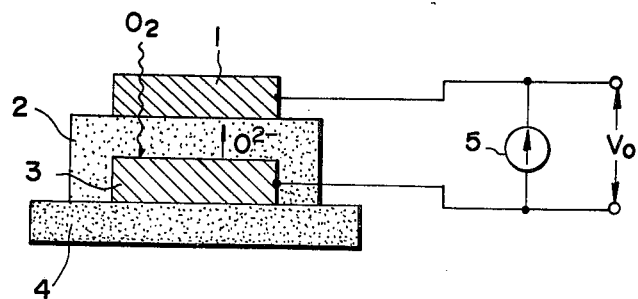
FIG. 1 is a schematic illustration of a conventional air-fuel ratio detecting apparatus.
Figure 2:
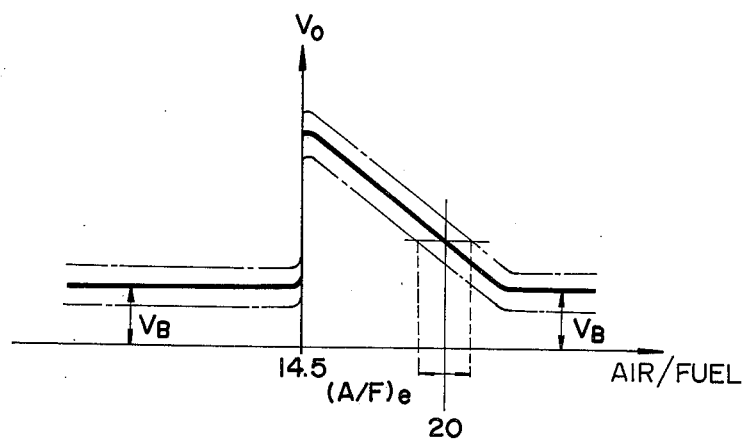
FIG. 2 is a graph showing the voltage output characteristics of the apparatus of FIG. 1 in terms of air/fuel ratio.

As a detecting apparatus for detecting the air-fuel ratio in the rich or lean air-fuel mixture range, a conventional apparatus shown in FIG. 1 has already been proposed and includes a measuring electrode 1 made of platinum, a porous solid electrolyte layer 2, a reference electrode 3, and a protective layer 4 which are successively piled up, and further includes a constant-current power source for supplying a bias current across the electrodes 1 and 3. This is disclosed in the pending application of Shinji Kimura et al, U.S. Patent Application Ser. No. 28,747, filed on Apr. 10, 1979 and entitled "Method of Detecting Air/Fuel in Combustor by Detecting Oxygen in Combustion Engine", new U.S. Pat. No. 4,224,113. This apparatus exhibits an output characteristic shown in FIG. 2. With such a conventional air-fuel ratio detecting apparatus, oxygen diffused into an electrode is carried in the form of ions to the another electrode by supplying a bias current, in order to produce an oxygen partial pressure serving as a reference. The solid electrolyte 2 is used as a passage through which oxygen ions are permeable under the action of the bias current, and also as a passage through which oxygen ions in exhaust gas are diffused into the reference electrode 3. As a result, an output voltage $V_o$ obtained as a detected output corresponds to a voltage which is obtained, as shown in FIG. 2, by adding an electromotive force dependent upon the difference in oxygen partial pressure between the electrodes 1 and 3, to a voltage $V_B$ which is decided by the product of the value of the bias current and the value of resistance of the solid electrolyte.

As will be appreciated, the voltage $V_B$ dependent on the resistance of the solid electrolyte 2 is prevented from scattering in output characteristics with respect to respective air-fuel ratio detecting apparatuses, by making the resistance values of the solid electrolyte 2 constant during production of the apparatuses. However, the solid electrolyte is prepared by firing a formed unfired paste, and therefore it is difficult to maintain constant the thickness and density which are in close relation to the resistance value. Thus, scattering in the resistance value of the solid electrolyte is unavoidably caused with respect to respective produce air-fuel ratio detecting apparatuses. Hence, when a bias current is supplied, such scattering in resistance value is directly converted to scattering in output voltage $V_B$ as indicated by a range between dash-dot lines in FIG. 2. This scattering range causes an error in air-fuel ratio measurement within a considerably wide range indicated by (A/F)e in FIG. 2. In this regard, since such scattering is of output voltage, it is necessary to use means for making constant the voltage $V_B$ dependent on the resistance of the solid electrolyte, particularly in case of air-fuel ratio control in a so-called lean-burn engine which is operated on an air-fuel ratio (Air/Fuel) higher than 20 in which a control accuracy of ±0.5 (in Air/Fuel valve) is required. This makes an air-fuel ratio control system complicated.

DETAILED DESCRIPTION OF THE INVENTION

Figure 3:
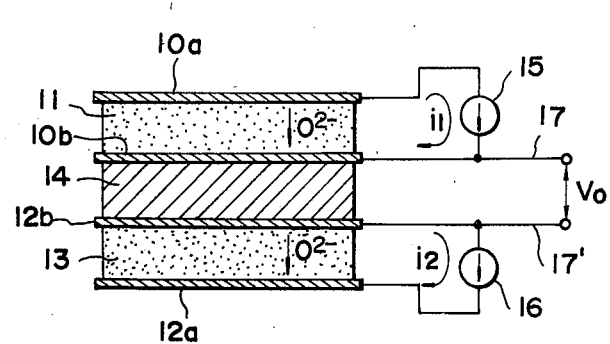
FIG. 3 is a schematic illustration of an air-fuel ratio detecting apparatus according to the present invention.

Referring now to FIG. 3 of the drawings, there is schematically shown an essential configuration of an air-fuel ratio detecting apparatus in accordance with the present invention. The apparatus comprises a pair of measuring electrodes 10a and 10b which are made of an electrically conductive material such as platinum, which is catalytically active on oxidation reactions of unburned gas or constituents in exhaust gas from an internal combustion engine. A porous solid electrolyte 11 is interposed between the pair of electrodes 10a and 10b. A pair of reference electrodes 12a and 12b are made of an electrically conductive material which is catalytically active. A porous solid electrolyte 13 is interposed between the reference electrodes 12a and 12b. A dense solid electrolyte 14 is interposed between the measuring electrode 10b and the reference electrode 12b. A measuring electrode section is constituted by the measuring electrodes 10a, 10b and the solid electrolyte 11. A reference electrode section is constituted by the reference electrodes 12a, and 12b and the solid electrolyte 13. The above-mentioned term "porous" in the solid electrolytes 11 and 13 means a structure through which oxygen molecules in exhaust gas are permeable by diffusion, whereas the above-mentioned term "dense" in the solid electrolyte 14 means a structure through which oxygen molecules in exhaust gas are not permeable even by diffusion.

A first constant-current power source 15 is electrically connected between the measuring electrodes 10a and 10b so as to cause a predetermined bias current $i_1$ to flow from the electrode 10b toward the electrode 10a. A second constant-current power source 16 is electrically connected between the reference electrodes 12a and 12b so as to cause a predetermined bias current $i_2$ to flow from the electrode 12a toward the electrode 12b. It is to be noted that the relationship between the bias currents $i_1$ and $i_2$ is $i_1 > i_2$ or $i_1 < i_2$. With this arrangement, an output voltage $V_0$ is picked up through leads 17 and 17' which are connected respectively to the measuring electrode 10b and the reference electrode 12b which are disposed at the two side surfaces of the solid electrolyte, so as to obtain the output voltage which varies generally linearly on the variation of air-fuel ratio in the rich or lean air-fuel mixture range.

The manner of operation of the thus arranged air-fuel ratio detecting apparatus according to the present invention will be explained hereinafter.

Figure 4:
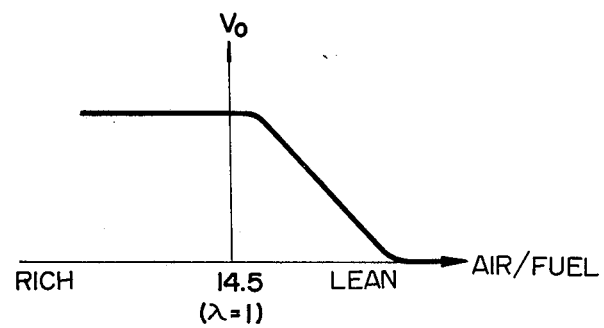
FIGS. 4 and 5 are graphs showing the voltage output characteristics of the apparatus of FIG. 3 in terms of air/fuel ratio.

When the relationship between the bias currents produced by the constant-current power sources 15 and 16 is $i_1 > i_2$, the output voltage $V_0$ is saturated as shown in FIG. 4 to a constant value in the rich air-fuel mixture range and gradually lowered in the lean air-fuel mixture range beyond the stoichiometric air-fuel ratio or Air/Fuel valve (14.5 corresponding to an Air Excess Ratio = 1), so that the output voltage $V_0$ finally becomes zero. Thus, the characteristics of the output voltage $V_0$ indicated in FIG. 4 are obtained.

The operation to obtain the output characteristics shown in FIG. 4 will be explained further in detail as follows: the oxygen partial pressure in exhaust gas is in a range of $10^{-2}$–$10^{-3}$ atm. in both the rich and lean air-fuel mixture ranges. Additionally, it is known that the amount of unburned gas such as hydrocarbon (HC) and carbon monoxide (CO) contained in exhaust gas is larger in the rich air-fuel mixture range and abruptly decreased in the lean air-fuel ratio range when exceeding the stoichiometric air-fuel ratio.

At the measuring electrode section, oxygen molecules diffused in the electrode 10a are moved in the form of ion O⁻⁻ (indicated by $O^{2-}$ from the electrode 10a toward the electrode 10b in the opposite direction of the flow of the bias current $i_1$ by virtue of the bias current $i_1$. At the reference electrode section, oxygen molecules diffused in the electrode 12b are moved in the form of ion $O^{2-}$ from the electrode 12b to the electrode 12a in the opposite direction of the flow of the bias current $i_2$. As appreciated, the amount of oxygen taken out of the electrode 10a is larger than that of the electrode 12b. The oxygen ion $O^{2-}$ reaching the electrodes 10b and 12a are changed into the form of oxygen molecules, serving to make oxygen partial pressure high in the electrodes 10b and 12a.

Upon the above-mentioned premise, the operation in the rich air-fuel mixture range whose A/F value is lower than 14.5 will be explained.

Since a larger amount of unburned gas such as HC and CO is contained in exhaust gas in the rich air-fuel mixture range, oxidation reaction of the unburned gas under catalytic action takes place on the surface of the electrodes 10a and 12a which contact the exhaust gas, in which unburned constituents such as HC and CO combine with oxygen in the exhaust gas. By this oxidation reaction consuming oxygen, the oxygen partial pressures in the electrodes 10a and 12a are lowered to a low level of approximately $10^{-15}$–$10^{-30}$ atm. Although oxygen in the exhaust gas is diffused through the solid electrolytes 11 and 13 into the electrodes 10b and 12b, the oxygen partial pressures in these electrodes 10b and 12b is similarly at a low level such as approximately $10^{-15}$–$10^{-30}$ atm. The above-mentioned operation is in the case where bias current is not taken into consideration. However, according to the present invention, the bias currents $i_1$ and $i_2$ ($i_1 > i_2$) are supplied respectively by the constant-current power source 15 and 16. Accordingly, at the measuring electrode section, the oxygen ion $O^{2-}$ carried from the electrode 10a acts to increase the oxygen partial pressure in the electrode 10b. At the reference electrode section, the oxygen diffused in the electrode 12b is taken out in the form of ion $O^{2-}$.

This results in the condition where the oxygen partial pressure in the measuring electrode 10b is higher than in the reference electrode 12b, which is caused by the solid electrolyte 14 interposed therebetween. This condition is maintained in the entire rich air-fuel mixture range. Hence, an electromotive force corresponding to the difference between the oxygen partial pressures is developed between the electrodes 10b and 12b, which electromotive force is picked up through the leads 17 and 17' as the output voltage $V_o$ which will be saturated to become a constant voltage in the rich air-fuel mixture range.

Subsequently, the operation in the lean air-fuel mixture range whose Air/Fuel value is higher than 14.5 will be explained.

When the Air/Fuel value comes into the lean air-fuel mixture range exceeding the stoichiometric air-fuel ratio (Air/Fuel value = 14.5), the amount of unburned gas in the exhaust gas abruptly decreases. Accordingly, the consumption of oxygen by oxidation reaction does not occur at the electrodes 10a and 12a, and therefore the oxygen partial pressures at the electrodes 10a and 12a become at approximately equal levels to that in the exhaust gas, approximately i.e., $10^{-2}$–$10^{-3}$ atm. As a result, the oxygen partial pressure in the electrode 10b of the measuring electrode section abruptly increases to a level of approximately $10^{-2}$–$10^{31\ 3}$ atm. under the action of oxygen carried in the form of ions by the bias current and oxygen diffused through the solid electrolyte. To the contrary, the oxygen partial pressure in the electrode 12b of the reference electrode section gradually increases with increase in Air/Fuel value. In other words, at an Air/Fuel value in the vicinity of stoichiometric or 14.5, the supply amount of oxygen by diffusion is smaller than the amount of oxygen consumed in the form of ion by the bias current $i_2$, so that the oxygen partial pressure in the electrode 12b is lower. When the Air/Fuel value increases, the oxygen amount consumed by diffusion gradually increases though the oxygen amount taken out in the form of ions is constant, and therefore the oxygen partial pressure in the electrode 12b increases in dependence on increase in the Air/Fuel value. As a result, the difference in oxygen partial pressure of the electrode 12b from the electrode 10b is gradually decreased so as to obtain the characteristic of the output voltage $V_o$ which varies generally linearly at the lean air-fuel mixture range as shown in FIG. 4. When the A/F value further increases, the oxygen partial pressure in the electrode 12b becomes equal to that in the electrode 10b, accordingly the difference between the oxygen partial pressures becomes zero. As a result, no electromotive force is developed so that the output voltage $V_o$ becomes zero.

As will be apparent from the above-mentioned operation, since the air-fuel ratio detecting apparatus according to the present invention is arranged so that the bias current is not supplied to the solid electrolyte 14 which develops an electromotive force corresponding to the difference between the oxygen partial pressures of the electrodes 10b and 12b, the electromotive force corresponding to the difference in oxygen partial pressure generated between the electrodes 10b and 12b can be picked up as it is as the output voltage $V_o$. The output voltage $V_o$ is never affected by the resistance value of the solid electrolyte 14, and therefore, if a variety of resistance values of solid electrolytes 14 occur due to scattering of thickness and the like caused by mass production of the solid electrolytes, the scattering in output voltages among air-fuel ratio detecting apparatuses does not occur, which makes possible the mass production air-fuel ratio detecting apparatuses which are excellent in quality.

Figure 5:
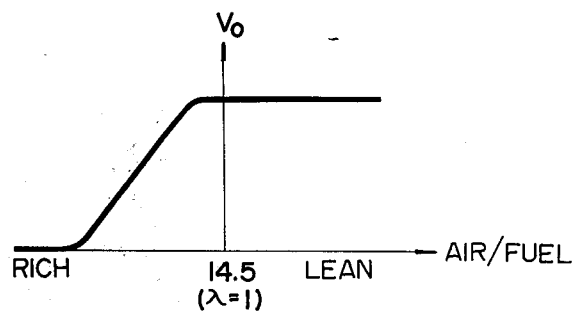

FIG. 5 shows the variation of output voltage $V_o$ as a function of the variation of the Air/Fuel value when the relationship between the two kinds of the bias currents is changed to $i_1 < i_2$ in the embodiment of FIG. 3. As shown, the output voltage $V_o$ is saturated to a constant value, and its characteristics vary to be inclined when the Air/Fuel value is lowered into the rich air-fuel mixture range beyond the stoichiometric Air/Fuel value or 14.5. In other words, by changing the relationship between the bias current into $i_1 < i_2$, the amount of oxygen consumed by taking out in the form of ions from reference electrode 12b by means of bias current $i_2$ becomes larger than the amount of oxygen supplied in the form of ions to the measuring electrodes 10b by means of the bias current $i_1$.

Upon deciding the bias currents $i_1$ and $i_2$ as mentioned above, the oxygen partial pressure in the reference electrode 12b is at a low value of approximately $10^{-15}$–$10^{-30}$ atm. throughout all the lean and rich air-fuel mixture ranges since the amount of oxygen consumed in the form of ions by the bias current $i_2$ is larger, whereas the oxygen partial pressure in the measuring electrode 10b is at a value of approximately $10^{-2}$–$10^{-3}$ atm. which is the same as the value of the oxygen partial pressure in the exhaust gas, so that an electromotive force is developed to produce the output voltage $V_o$. When the Air/Fuel value lowers to enter the rich air-fuel mixture range, the amount of oxygen supplied to the electrode 10b due to diffusion is decreased by the oxidation reaction of the unburned gas. The decrease in the amount of supplied oxygen causes the oxygen partial pressure in the electrode 10b to gradually decrease, so that the inclined characteristic of output voltage $V_o$ is obtained at the rich air-fuel mixture range. Finally, the oxygen partial pressure in the electrode 10b is also lowered to a level of approximately $10^{-15}$–$10^{-30}$ atm., and becomes equal to the level of the oxygen partial pressure in the electrode 12b. As a result, no electromotive force is developed so that the output voltage $V_o$ becomes zero.

While the above-discussed embodiments have been arranged so that the measuring electrodes 10a, 10b and the reference electrodes 12a, 12b are respectively formed of an electrically conductive material which is catalytically active such as platinum, so as to exhibit oxidation catalytic action on unburned gas, it will be noted that the measuring electrodes 10a and 10b may be formed of an electrically conductive material which is catalytically inert so as not to exhibit catalytic action on the unburned gas. It is preferable to use as the catalytically inert, electrically conductive material an electrically conductive material such as Au, Ag, $SnO_2$, $V_2O_3$, or PbO, or perofskite type electrically conductive material such as $LaCrO_3$, $LaNiO_3$, or $SmCoO_3$ added with Ca, Zr, Mg, or Sr.

An arrangement in which the electrodes 10a and 10b are catalytically inert is also the same as that of FIG. 3, and additionally when the flow directions of the bias currents $i_1$ and $i_2$ are decided as indicated in FIG. 3, the output voltage characteristics of FIG. 4 are obtained, whereas in order to obtain the characteristics of FIG. 5, the polarities of the constant-current power sources 15 and 16 are changed with respect to each other so as to reverse the flow directions of the bias currents $i_1$ and $i_2$.

Now, the operation in the case where the measuring electrodes 10a and 10b are catalytically inert will be explained with reference to FIGS. 3 and 4. Since the oxygen partial pressure in the measuring electrode is not affected by an oxidation reaction under catalyst action, the bias current $i$ is decided so that the oxygen partial pressure is at a value of $10^{-2}$–$10^{-3}$ throughout all the rich and lean air-fuel mixture ranges.

The oxygen partial pressure in the reference electrode 12a is at a low level of approximately $10^{-15}$–$10^{-30}$ atm. in the rich air-fuel mixture range, because of the oxidation reaction of the unburned gas under catalytic action, and accordingly the output voltage $V_o$ is at a constant level. However, in the lean air-fuel mixture range, the amount of oxygen consumed by being taken out in the form of ions by means of the bias current $i_2$ is larger than the amount of oxygen supplied by oxygen diffusion at a relatively low Air/Fuel value stage, whereas the oxygen supply amount by diffusion gradually increases with the increase in Air/Fuel value. As a result, the oxygen partial pressure in the electrode 12b rises to obtain the characteristics of output voltage $V_o$ shown in FIG. 4 which characteristic is inclined at the lean air-fuel mixture range.

In the case where the flow directions of the bias currents $i_1$ and $i_2$ are made opposite to those shown in FIG. 3 in order to obtain the voltage output characteristics of FIG. 5, the amount of oxygen consumed in the form of ions from the measuring electrode 10b by means of the bias current $i_1$ is decided so that the oxygen partial pressure in the measuring electrode 10b becomes a low level of approximately $10^{-15}$–$10^{-30}$ atm.

The reference electrode 12b is supplied with oxygen which is fed by means of diffusion through the solid electrolyte 13 and carrying in the form of ions from the electrode 12a by the bias current $i_2$, and therefore the oxygen partial pressure in the reference electrode 12b is at a high value of approximately $10^{-2}$–$10^{-3}$ atm. in the lean air-fuel mixture range where the amount of unburned gas is smaller, thus developing an electromotive force whose output voltage $V_o$ is at a constant level. When the Air/Fuel value is lowered to enter the rich air-fuel mixture range, the amount of unburned gas increases, by which oxygen is consumed by oxidation reaction at the electrode 12a under catalytic action. Accordingly, the supply amount of oxygen carried to the reference electrode 12b in the form of ions is constant, whereas the supply amount of oxygen by diffusion gradually decreases with lowering in the Air/Fuel value. Therefore, the oxygen partial pressure in the reference electrode gradually lowers, and finally becomes a low level of approximately $10^{-15}$–$10^{-30}$ atm. which level is the same as in the measuring electrode 10b. Hence, the difference in oxygen partial pressure between the electrode 10b and 12b is reduced and consequently the output voltage $V_o$ lowers with lowering in the Air/Fuel value and finally becomes zero.

Figure 6:
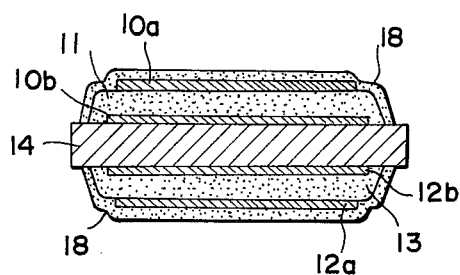
FIG. 6 is a cross-sectional view of an embodiment of the air-fuel ratio detecting apparatus according to the present invention.

FIG. 6 illustrates an embodiment of the air-fuel ratio detecting apparatus according to the present invention. A process for preparing the air-fuel ratio detecting apparatus is shown in FIG. 7.

Figure 7:
FIG. 7 is an illustration showing the process for preparing the apparatus of FIG. 6.
Figure 7:
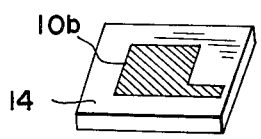
Figure 7:
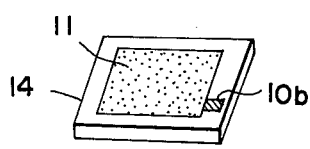
Figure 7:
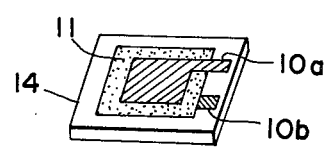
Figure 7:
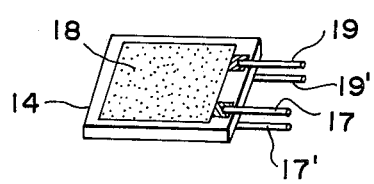

The construction of the apparatus of FIG. 6 will be apparent from the following description with reference to the preparing process of FIG. 7. At first, the measuring electrode 10b and the reference electrode 12b are formed by screen printing a platinum paste or a platinum containing paste, respectively, on both side surfaces of the solid electrolyte 14 in the form of a fired or unfired base plate made of an oxygen ion conductive solid electrolyte such as $ZrO_2$, $ThO_2$—$Y_2O_3$, or $CaO$—$Y_2O_3$ which is stabilized with, for example, CaO, $Y_2O_3$, or MgO. Then, the solid electrolytes 11 and 13 are formed by screen printing, excepting sections to which connecting electrode leads are connected. The materials of the solid electrolyte 11 and 13 are the same as that of the solid electrolyte 14, but the particle size of the solid electrolytes is about 0.5 micron which is larger than of the solid electrolyte 14. Further, the measuring electrode 10a and the reference electrode 12a are formed by screen printing a platinum paste or a platinum containing paste, respectively, on the surface of solid electrolyte 11 and 13. After protective layers 18 are by formed screen printing, the resultant article is fired at 1450° C. The formation of the protective layer 18 is carried out by screen printing a paste of, for example, $ZrO_2$—CaO, $Al_2O_3$, MgO, or spinel. Finally, electrode leads 17, 17' and 19, 19' formed of, for example, a platinum wire are welded in positions to obtain a complete body section of the air-fuel detecting apparatus.

Alternately, the electrodes 10a, 10b, 12a and 12b may be formed on the surface of the solid electrolyte by sputtering, or flash plating. Additionally, the porous solid electrolytes 11, 13 and the protective layers 18 may be formed by plasma spraying. Such a preparing process is effective in the case where the measuring electrodes 10a and 10b are formed of a catalytically inert, electrically conductive material which cannot stand against the firing temperature of the solid electrolyte 14.

Figure 8:
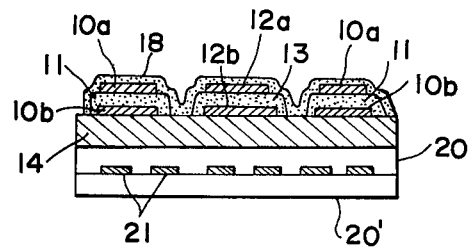
FIG. 8 is a cross-sectional view of another embodiment of the air-fuel ratio detecting apparatus according to the present invention.
Figure 9:
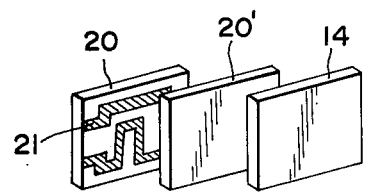
FIG. 9 is an illustration showing the process for preparing the apparatus of FIG. 8.
Figure 9:
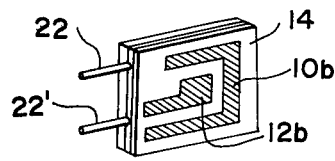
Figure 9:
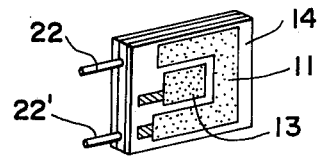
Figure 9:
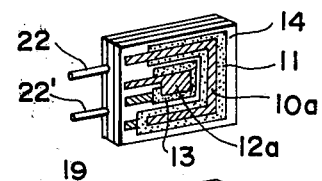
Figure 9:
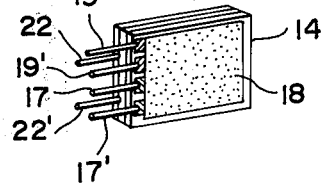

FIG. 8 illustrates another embodiment of the air-fuel ratio detecting apparatus according to the present invention. A process for preparing the apparatus is shown in FIG. 9. The construction of the apparatus will become apparent from the following description with reference to FIG. 9. At first, a heater 21 is formed on one side surface of an alumina base plate 20 by screen printing a platinum paste. Then, another alumina base plate 20' and the solid electrolyte 14 are forced to contact with the alumina base plate 20, inserting leads 22, 22' to contact with the heater 21, so as to obtain an integral base section. The measuring electrode 10b and the reference electrode 12b are formed on the surface of solid electrolyte 14 of the thus formed integral base section by screen printing platinum pastes. The porous solid electrolyte 11 and 13 are formed respectively on the surface of the thus formed electrodes 10b and 12b by screen printing. Further, the measuring electrodes 10a and 12b are formed respectively on the surfaces of the thus formed solid electrolytes 11 and 13 by screen printing platinum pastes. Subsequently, the protective layer 18 is formed by screen printing so as to cover approximately the entire surface of the solid electrolyte 14. After firing the thus formed article at 1450° C., the leads 17, 17' and the leads 19, 19' are connected to the corresponding electrodes.

Alternately, the air-fuel ratio detecting apparatus indicated in FIG. 8 may be prepared by the following process: After the alumina base plates 20 and 20' are piled and forced to contact each other, the resultant integral base section is fired. The measuring electrode 10b and the reference electrode 12b are formed on the surface of the fired integral base section by sputtering, flash plating, or screen printing. Subsequently, the solid electrolytes 11 and 13 are formed by screen printing on the surface of the thus formed measuring and reference electrodes, with the measuring electrode 10a being and the reference electrode 12a formed by sputtering, or flash plating. Thereafter, the protective layer 18 is formed by plasma spraying, and finally the leads 17, 17' and the leads 19, 19' are connected to the corresponding electrodes.

It will be understood that the materials of the parts and elements shown in FIG. 8 are the same as those of the corresponding ones in FIG. 6. The body section of the air-fuel ratio detecting apparatus shown in FIG. 8 is arranged so as to flow a certain electric current through the heater 21 which is interposed between the alumina base plates 20 and 20', and consequently the temperature of the body section of the apparatus is maintained at a constant level, without being affected by exhaust gas temperature by virtue of heat generated by the heater. Therefore, the internal resistance and the gas diffusion constant of the solid electrolytes 11 and 13 dependent on temperature becomes constant, respectively, which results in more stable voltage output characteristics.

As will be appreciated from the above, according to the present invention, a section at which an electromotive force is generated is disposed so as to be separate from a section for carrying oxygen ions by flowing a bias current. In this way a bias current is caused to flow through the electromotive force generating section and accordingly output voltage is never affected by voltage drop due to the resistance of a solid electrolyte. Therefore, the voltage output characteristics are not affected by scattering in resistance values of the solid electrolyte caused during production of the solid electrolyte. This makes it possible to obtain air-fuel ratio detecting apparatuses having uniform characteristics even by mass production, thereby attaining a high accuracy air-fuel ratio control at air-fuel mixture ranges out of the stoichiometric air-fuel ratio by a simple closed loop control system.

What is claimed is:

1. An air-fuel ratio detecting apparatus, comprising:
a first pair of electrodes;
a first porous solid electrolyte interposed between said first pair of electrodes;
a second pair of electrodes;
a second porous solid electrolyte interposed between said second pair of electrodes;
a dense solid electrolyte with which one of said first pair of electrodes and one of said second pair of electrodes is in contact;
means for causing constant-currents to flow through said first and second pairs of electrodes, respectively; and
means for detecting voltage developed between said electrodes contacting with said dense solid electrolyte.

2. An air-fuel ratio detecting apparatus as claimed in claim 1, in which at least one of said first pair of electrodes is made of platinum, and at least one of said second pair of electrodes is made of platinum.

3. An air-fuel ratio detecting apparatus as claimed in claim 1, in which said first and second pair of electrodes are formed of a material which is catalytically active.

4. An air-fuel ratio detecting apparatus as claimed in claim 1, in which said first pair of electrodes are formed of a material which is catalytically inert.

5. An air-fuel ratio detecting apparatus as claimed in claim 4, in which the catalytically inert material comprises a material selected from the group consisting of Au, Ag, $SnO_2$, $V_2O_3$, PbO, $LaCrO_3$, $LaNiO_3$, and $SmCoO_3$.

6. An air-fuel ratio detecting apparatus as claimed in claim 1, in which said constant-current flowing means includes first means for causing a first bias current to flow through said first pair of electrodes, and second means for causing a second bias current the flow through said second pair of electrodes.

7. An air-fuel ratio detecting apparatus as claimed in claim 6, in which said constant-current flowing means includes means for setting said bias current to said first pair of electrodes greater than said bias current to said second pair of electrodes.

8. An air-fuel ratio detecting apparatus as claimed in claim 6, in which said constant-current flowing means includes means for setting said bias current to said first pair of electrodes lower than said current to said second pair of electrodes.

9. An air-fuel ratio detecting apparatus as claimed in claim 1, wherein said first and second porous solid electrolytes are the same in material as said dense solid electrolyte.

10. An air-fuel ratio detecting apparatus as claimed in claim 9, in which said first and second porous solid electrolytes are larger in the particle size of their material than said dense solid electrolyte.

11. An air-fuel ratio detecting apparatus as claimed in claim 9, wherein said material of said first and second porous solid electrolytes comprises a material selected from the group consisting of $ZrO_2$, $ThO_2$—$Y_2O_3$, and $CaO$—$Y_2O_3$.

12. An air-fuel ratio as claimed in claim 1, further comprising a protective layer to cover said first and second pairs of electrodes and said first and second porous solid electrolytes.

13. An air-fuel ratio detecting apparatus as claimed in claim 12, in which said protective layer is formed of a material comprising a material selected from the group consisting of $ZrO_2$—CaO, $Al_2O_3$ and MgO.

14. An air-fuel ratio detecting apparatus as claimed in claim 1, further comprising means, including an electrical resistance element, for heating said solid electrolytes.

15. An air-fuel ratio detecting apparatus as claimed in claim 14, further comprising a base plate of alumina directly contacting with said dense solid electrolyte, in which said heating means contacts with said base plate.

* * * * *